United States Patent
Garcia-Sastre et al.

(10) Patent No.: US 8,709,442 B2
(45) Date of Patent: Apr. 29, 2014

(54) RECOMBINANT NEGATIVE STRAND VIRUS RNA EXPRESSION SYSTEMS AND VACCINES

(75) Inventors: Adolfo Garcia-Sastre, New York, NY (US); Peter Palese, Leonia, NJ (US)

(73) Assignee: ICAHN School of Medicine at Mount Sinai, New York, NY (US)

( * ) Notice: Subject to any disclaimer, the term of this patent is extended or adjusted under 35 U.S.C. 154(b) by 243 days.

(21) Appl. No.: 10/505,613

(22) PCT Filed: Feb. 21, 2003

(86) PCT No.: PCT/US03/05353
§ 371 (c)(1),
(2), (4) Date: May 17, 2005

(87) PCT Pub. No.: WO03/072725
PCT Pub. Date: Sep. 4, 2003

(65) Prior Publication Data
US 2005/0221489 A1    Oct. 6, 2005

(51) Int. Cl.
*A61K 39/155*    (2006.01)
*C12N 15/67*    (2006.01)

(52) U.S. Cl.
USPC .................................... 424/211.1; 435/69.1

(58) Field of Classification Search
USPC .............. 435/320.1, 91.41, 91.42; 424/209.1, 424/211.1, 213.1, 212.1, 224.1
See application file for complete search history.

(56) References Cited

U.S. PATENT DOCUMENTS

| | | | | |
|---|---|---|---|---|
| 5,166,057 A | * | 11/1992 | Palese et al. | 435/69.1 |
| 5,578,473 A | * | 11/1996 | Palese et al. | 435/235.1 |
| 5,786,199 A | * | 7/1998 | Palese | 435/239 |
| 5,820,871 A | * | 10/1998 | Palese et al. | 424/209.1 |
| 5,854,037 A | * | 12/1998 | Palese et al. | 435/455 |
| 6,001,634 A | * | 12/1999 | Palese et al. | 435/235.1 |
| 6,136,585 A | * | 10/2000 | Ball et al. | 435/236 |
| 6,146,642 A | * | 11/2000 | Garcia-Sastre et al. | 424/214.1 |
| 6,451,323 B1 | * | 9/2002 | Garcia-Sastre et al. | 424/214.1 |
| 6,544,785 B1 | * | 4/2003 | Palese et al. | 435/325 |
| 6,649,372 B1 | * | 11/2003 | Palese et al. | 435/69.1 |
| 6,887,699 B1 | * | 5/2005 | Palese et al. | 435/239 |

OTHER PUBLICATIONS

Whelan et al. ( Proc. Natl. Acad. Sci. USA, 1995, vol. 92, pp. 8388-8392.*
Feit et al. 2003, J. Pat. Trade. Off. Soc., vol. 85, No. 1, pp. 5-21.*
Fields et al. Published in 1996 by Lippinocott-Raven Publishers, chapter 40, pp. 1177-1179 & 1190-1193.*
Nakaya al. J. Virol. Dec. 2001, vol. 75, No. 23, pp. 11868-11873.*
Bukreyev et al. J. Virol. 1996, vol. 70, No. 10, pp. 6634-6641.*
Romer-Oberdorfer et al. J. Gene. Virol. 1999, vol. 80, pp. 2987-2995.*
Krishnamurthy et al. Virol. 2000, vol. 278, pp. 168-182.*
Huang et al. J. Gene. Virol. 2001, vol. 82, pp. 1729-1736.*
Garcia-Saster et al. (A) J. Virol. 1994, vol. 68, No. 10, pp. 6254-6261.*
Peeters et al. J. Virol. 1999, vol. 73, No. 6, pp. 5001-5009.*
Robert et al. Virology, 1998, vol. 471, pp. 1-6.*
Neumann et al. JGV, 2002, vol. 83, No. 11, pp. 2635-2662.*
Takeda, M. et al (2006) Journal of Virology vol. 80: 4242-4248.
Gao, Q. et al (2008) Journal of Virology Vo. 82: 2692-2698.

* cited by examiner

*Primary Examiner* — Bao Li
(74) *Attorney, Agent, or Firm* — Klauber & Jackson LLC (57) ABSTRACT

The present invention relates to recombinant RNA virus templates derived from and applicable to negative strand naturally non-segmented viruses, including the families Bornaviridae, Filoviridae, and Paramyxoviridae, and methods for generating such recombinant RNA virus templates, wherein the templates are generated from two or more recombinant RNA molecules. The invention relates to the use of segmented recombinant RNA virus templates for naturally non-segmented RNA viruses to express heterologous gene products in appropriate host cell systems and/or to construct recombinant viruses taken from that family and that express, package, and/or present the heterologous gene product. The invention includes the expression products and recombinant and chimeric viruses thus prepared and vaccine and therapeutic formulations comprising the recombinant RNA viruses.

6 Claims, 2 Drawing Sheets

Wild-type NDV non-segmented genome

Example of the genome of a segmented NDV vector

RECOMBINANT NEGATIVE STRAND VIRUS RNA EXPRESSION SYSTEMS AND VACCINES

BACKGROUND OF THE INVENTION

1. Field of the Invention

The present invention relates to recombinant RNA virus templates derived from and applicable to negative strand naturally non-segmented viruses, including the families Bornaviridae, Filoviridae, and Paramyxoviridae, and methods for generating such recombinant RNA virus templates, wherein the templates are generated from two or more recombinant RNA molecules. The recombinant RNA virus templates may be used to express heterologous gene products in appropriate host cell systems and/or to construct recombinant viruses taken from that family and that express, package, and/or present the heterologous gene product. The expression products and chimeric viruses thus prepared may advantageously be used in vaccine formulations. The present invention also relates to the corresponding genetically engineered recombinant viruses which contain modifications and/or mutations that make the recombinant virus suitable for use in vaccine and therapeutic formulations, such as an attenuated phenotype or enhanced immunogenicity.

2. Description of the Related Art

A number of DNA viruses have been genetically engineered to direct the expression of heterologous proteins in host cell systems (e.g., vaccinia virus, baculovirus, etc.). Similar advances have been made with positive-strand RNA viruses (e.g., poliovirus). The expression products of these constructs, i.e., the heterologous gene product or the chimeric virus which expresses the heterologous gene product, are thought to be potentially useful in vaccine formulations (either subunit or whole virus vaccines). One drawback to the use of viruses such as vaccinia for constructing recombinant or chimeric viruses for use in vaccines is the lack of variation in its major epitopes. This lack of variability in the viral strains places strict limitations on the repeated use of chimeric vaccinia, in that multiple vaccinations will generate host-resistance to the strain so that the inoculated virus cannot infect the host. Inoculation of a resistant individual with chimeric vaccinia will, therefore, not induce efficient immune stimulation.

By contrast, the negative-strand RNA viruses, would be attractive candidates for constructing chimeric viruses for use in vaccines. The negative-strand RNA viruses are desirable because the genetic variability or multiple serotypes of some negative-strand viruses, influenza, for example, allows for the construction of a repertoire of vaccine formulations which stimulate immunity without risk of developing a tolerance. Construction of infectious recombinant or chimeric negative-strand RNA particles was achieved with the influenza virus (U.S. Pat. No. 5,166,057 to Palese et al., incorporated herein by reference in its entirety). Additionally, the use of viruses which are not natural pathogens of humans, while they may be able to infect humans, is attractive because of the lack of pre-existing immunity in humans. Examples of negative-strand RNA viruses which are not natural pathogens of humans, but which can infect humans, include for example Newcastle disease virus (NDV), vesicular stomatitis virus (VSV), bovine respiratory syncytial virus (RSV) and avian pneumoviruses.

Non-Segmented Viruses

Virus families containing enveloped single-stranded RNA of the negative-sense genome are classified into groups having non-segmented genomes (Paramyxoviridae, Rhabdoviridae, Bornaviridae and Filoviridae) or those having segmented genomes (Orthomyxoviridae, Bunyaviridae and Arenaviridae). The Paramyxoviridae family, described in detail below, and used in the examples herein, includes the viruses of Newcastle disease virus (NDV), parainfluenza virus, Sendai virus, simian virus 5, measles virus and mumps virus. The Rhabdoviridae family includes the viruses rabies virus and vesicular stomatitis virus (VSV). The following discussion focuses on a particular member of the Paramyxoveridae family by way of illustration and not limitation.

Newcastle disease virus (NDV) is a negative strand RNA virus which belongs to the genus *Rubulavirus* of the family Paramyxoviridae, of the order of the Mononegavirales. This virus is an avian pathogen and several NDV strains have been isolated which are characterized by different levels of virulence in birds. Virulent (velogenic) strains of NDV cause a highly pathogenic disease in poultry. However, avirulent (mesogenic and lentogenic) strains of NDV cause mild or asymptomatic infections and they are currently used as live vaccines in domestic poultry against Newcastle disease. Humans are not the usual hosts for NDV, but the virus has been administered to humans and been found to be safe (Emmerson, P. T. (1994) In Webster R G, Granoff A (ed), Encyclopedia of Virology. Academic Press, London; Lorence R M et al. (1994) Cancer Res 54: 6017-6021).

The Newcastle disease virus, a representative member of the Paramyxoviridae family, is an enveloped virus containing a linear, single-strand, nonsegmented, negative sense RNA genome. The molecular organization of the NDV genome is similar to that of other Paramyxoviridae and Rhabdoviridae viruses. The genomic RNA contains genes in the order of 3'-NP-P-M-F-HN-L-5'. The genomic RNA also contains a leader sequence at the 3' end. Sequences at the end of the genome are involved in transcription and replication of the RNA by the viral RNA-dependent RNA polymerase. In addition, intergenic junctions contain gene-end, polyadenylation and gene-start signals.

The structural elements of the virion include the virus envelope which is a lipid bilayer derived from the cell plasma membrane. The glycoprotein, hemagglutinin-neuraminidase (HN), protrudes from the envelope allowing the virus to contain both hemagglutinin and neuraminidase activities. The fusion glycoprotein (F), which also interacts with the viral membrane, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the nucleocapsid is the nucleocapsid protein (NP) which confers helical symmetry on the capsid. In association with the nucleocapsid are the P and L proteins. The phosphoprotein (P), which is subject to phosphorylation, is thought to play a regulatory role in transcription. The L gene, which encodes an RNA-dependent RNA polymerase, is required for viral RNA synthesis together with the P protein. The L protein, which takes up nearly half of the coding capacity of the viral genome is the largest of the viral proteins, and plays an important role in both transcription and replication.

The replication of all negative-strand RNA viruses, including NDV, is complicated by the absence of cellular machinery required to replicate RNA. Additionally, the negative-strand genome cannot be translated directly into protein, but must first be transcribed into a positive-strand (mRNA) copy. Therefore, upon entry into a host cell, the genomic RNA alone cannot synthesize the required RNA-dependent RNA polymerase. The L, P and NP proteins must enter the cell along with the genome on infection.

It is hypothesized that most or all of the viral proteins that transcribe NDV mRNA also carry out their replication. The mechanism that regulates the alternative uses (i.e., transcription or replication) of the same complement of proteins has not been clearly identified but appears to involve the abundance of free forms of one or more of the nucleocapsid proteins, in particular, the NP. Directly following penetration of the virus, transcription is initiated by the L protein using the negative-sense RNA in the nucleocapsid as a template. Viral RNA synthesis is regulated such that it produces monocistronic mRNAs during transcription.

Following transcription, virus genome replication is the second essential event in infection by negative-strand RNA viruses. As with other negative-strand RNA viruses, virus genome replication in Newcastle disease virus (NDV) is mediated by virus-specified proteins. The first products of replicative RNA synthesis are complementary copies (i.e., plus-polarity) of NDV genome RNA (cRNA). These plus-stranded copies (anti-genomes) differ from the plus-strand mRNA transcripts in the structure of their termini. Unlike the mRNA transcripts, the anti-genomic cRNAs are not capped and methylated at the 5' termini, and are not truncated and polyadenylated at the 3' termini. The cRNAs are coterminal with their negative strand templates and contain all the genetic information in each genomic RNA segment in the complementary form. The cRNAs serve as templates for the synthesis of NDV negative-strand viral genomes (vRNAs).

Both the NDV negative strand genomes (vRNAs) and antigenomes (cRNAs) are encapsidated by nucleocapsid proteins; the only unencapsidated RNA species are virus mRNAs. For NDV, the cytoplasm is the site of virus RNA replication, just as it is the site for transcription. Assembly of the viral components appears to take place at the host cell plasma membrane and mature virus is released by budding.

Engineering Negative Strand RNA Viruses

Reverse genetics systems which allow the genetic manipulation of the NDV genome from recombinant or cloned DNA have been described (Peeters B P et al. (1999) J Virol 73: 5001-5009; Romer-Oberdorfer A et al. (1999) J Gen Virol 80: 2987-2995; Krishnamurthy S et al. (2000) Virology 278: 168-182; Nakaya T et al. (2001) J Virol 75: 11868-11873). Recombinant systems for other non-segmented negative strand RNA viruses have also been described, including rabies virus (Schnell M J et al. (1994) EMBO J. 13: 4195-4203), VSV (Lawson N D et al. (1995) Proc Natl Acad Sci USA 92: 4477-4481; Whelan S P et al. (1995) Proc Natl Acad Sci (USA) 92: 8388-8392), measles virus (Radecke F et al. (1995) EMBO J. 14: 5773-5784), infectious human respiratory syncytial virus (Collins P L et al. (1995) Proc Natl Acad Sci (USA) 92: 11563-11567), Sendai virus (Garcin D et al. (1995) EMBO J. 14: 6087-6094; Kato A et al. (1996) Genes Cells 1: 569-579), rinderpest virus (Baron M D and Barrett T. (1997) J Virol 71: 1265-1271), parainfluenza virus (Hoffman M A, and Banerjee A K. (1997) J Virol 71: 4272-4277; Durbin A P et al. (1997) Virology 235: 323-332) and paramyxovirus SV5 (He B et al. (1997) Virology 1997; 237: 249-260). In all these systems, the necessary viral proteins of the non-segmented genome (NP, P/V, M, F, HN and L) are encoded from a single plasmid or recombinant nucleic acid on a single RNA molecule, thus mimicking the viral genome organization. In addition, the viral NP, P and L proteins were expressed from cotransfected plasmids or their function provided by co-expressed heterologous RNA polymerase or by helper virus.

Recombinant systems have also been developed for the segmented negative-strand RNA viruses, including particularly influenza A virus, which had presented an initial challenge to recombinant expression by virtue of the complex segmented nature of the virus and viral component expression (Neumann et al (1999) Proc. Natl. Acad. Sci. USA 96:9345-9350; Hoffmann E et al. (2000) Proc. Natl. Acad. Sci. USA 97:6108-6113; Fodor, E. et al. (1999) J Virol 73:9679-9682). In these cases, the necessary viral proteins of the segmented genome (PB1, PB2, PA, NP, M, HA, NA, and NS) are each encoded by distinct plasmids or by multiple plasmids expressing one or more viral protein encoded RNA.

SUMMARY OF THE INVENTION

The present invention relates to recombinant RNA virus templates derived from and applicable to negative strand naturally non-segmented viruses and methods for generating such recombinant RNA virus templates, wherein the templates are generated from two or more recombinant RNA molecules. Thus, the methods of the present invention are based on a change or alteration of the basic non-segmented nature of the genome of negative-strand naturally non-segmented RNA viruses to create plural genomic segments, to allow for rescue of a recombinant RNA virus containing a segmented genome. This then facilitates and is achieved by expression of the necessary viral proteins from multiple viral ribonucleoproteins instead of from a single viral non-segmented ribonucleoprotein.

The recombinant RNA virus templates of the present invention includes chimeric recombinant RNA virus templates wherein the chimeric virus templates are used to express heterologous gene products in appropriate host cell systems and/or to construct recombinant viruses that express, package, and/or present the heterologous gene product. The expression products and chimeric viruses thus prepared may advantageously be used in vaccine and therapeutic formulations.

The present invention also relates to the corresponding genetically engineered recombinant viruses wherein a naturally non-segmented virus is engineered to contain a segmented genome. The recombinantly segmented virus of the present invention may possess an altered or attenuated phenotype by virtue of the segmentation such that the virulence, for instance, of the virus may be altered. The invention further relates to genetically engineered recombinant viruses which contain modifications and/or mutations that make the recombinant virus suitable for use in vaccine formulations, such as an attenuated phenotype or enhanced immunogenicity.

The invention provides recombinant negative strand virus templates that are applicable to the Mononegavirales order, and that may include the families of Paramyxoviridae, Bornaviridae, Filoviridae and even Rhabdoviridae.

As an example of the Paramyxoviridae family, recombinant Newcastle disease virus (NDV) viral RNA templates are described wherein the six transcriptional units of NDV (NP, P, M, F, HN, and L) are divided into two or more segments, so that recombinant naturally non-segmented NDV virus is generated containing two or more RNA segments or recombinant RNA molecules.

The present invention provides a method for producing a negative-strand RNA virus for a negative-strand naturally non-segmented virus, comprising transfecting a host cell with:

(a) nucleotide sequences encoding two or more recombinant RNA molecules comprising a binding site for an RNA polymerase of a negative-strand RNA virus and signals required for viral-mediated replication and transcription and capable of expressing in said host cell genomic vRNA or corresponding cRNA for said virus; and (b) an expression vector or set of expression vectors capable of expressing a nucleoprotein and RNA-dependent polymerase for said virus; and recovering the virus from the culture.

Recombinant negative-strand viral RNA templates from recombinant negative-strand naturally non-segmented RNA viruses are described which may be used to express heterologous gene products in appropriate host cells and/or to rescue the heterologous gene in virus particles. In one embodiment, the invention relates to recombinant negative-strand viruses of the Paramyxoviridae or Rhabdoviridae families, including Newcastle disease virus, parainfluenza virus, Sendai virus, rabies virus, respiratory syncytial virus, measles virus, and mumps virus, which may be used to express one or more heterologous genes, including for instance heterologous viral genes, bacterial genes, parasites, genes of other pathogens, cancer antigens, oncogenes or modified oncogenes, genes encoding ligands, genes of therapeutic proteins, and genes for growth factors or immunomodulatory molecules. Examples of heterologous genes which can be expressed include for example, human immunodeficiency virus (IV) genes or antigens, hepatitis C virus (HCV) genes or antigens, RSV genes or antigens, parainfluenza virus genes, measles virus genes or antigens, malaria genes or antigens, *Pseudomonas* genes or antigens and *Mycobacterium tuberculosis* (TB).

The present invention provides a method for producing a chimeric negative-strand RNA virus for a negative-strand naturally non-segmented virus, comprising transfecting a host cell with:

(a) nucleotide sequences encoding two or more recombinant RNA molecules comprising a binding site for an RNA polymerase of a negative-strand RNA virus and signals required for viral-mediated replication and transcription and capable of expressing in said host cell genomic vRNA or corresponding cRNA for said virus and one or more heterologous RNA sequence; and (b) an expression vector or set of expression vectors capable of expressing a nucleoprotein and RNA-dependent polymerase for said virus; and recovering the chimeric virus from the culture.

The present invention relates to recombinant negative-strand naturally non-segmented viruses wherein the genome is segmented, including viruses of the Paramyxoviridae and Rhabdoviridae families, which contain modifications which result in phenotypes which make the recombinant virus more suitable for use in vaccine formulations, e.g., attenuated phenotypes and enhanced immunogenicity. The present invention relates to recombinant negative-strand viruses, including Newcastle disease viruses, measles viruses, mumps viruses, parainfluenza viruses, Sendai virus, and simian virus 5, which contain modifications which result in phenotypes which make the recombinant virus more suitable for use in vaccine formulations, e.g., attenuated phenotypes and enhanced immunogenicity.

In another embodiment, the present invention relates to engineering recombinant naturally non-segmented negative-strand viruses and viral vectors from two or more recombinant segments or viral nucleoproteins which further contain heterologous genes including, but not limited to, genes of other viruses, pathogens, cellular genes, tumor antigens, therapeutic proteins, ligands or receptor binding molecules, immunomodulatory molecules, etc.

In another embodiment, the present invention relates to engineering recombinant naturally non-segmented negative-strand RNA viruses and viral vectors for use as vaccines. The present invention relates to vaccine formulations suitable for administration to humans, as well as veterinary uses. The vaccines of the present invention may be designed for administration to domestic animals, including cats and dogs; wild animals, including foxes and racoons; livestock and fowl, including horses, cattle, sheep, turkeys and chickens.

In yet another embodiment, the invention relates to recombinant naturally non-segmented negative-strand RNA viral vectors and viruses from two or more recombinant segments or viral nucleoproteins which are engineered to encode mutant viral genes or to encode combinations of genes from different strains of the negative strand RNA virus.

The invention thus includes a set of two or more segmented recombinant RNA molecules comprising a binding site specific for an RNA polymerase of a naturally non-segmented RNA virus and signals required for said virus mediated replication and transcription, operatively linked to an RNA sequence, and collectively encoding the required functional transcriptional units of said RNA virus, wherein each encodes a subset of the required functional transcriptional units of said RNA virus.

Yet further, the invention extends to a set of two or more segmented recombinant RNA molecules comprising a binding site specific for an RNA polymerase of a naturally non-segmented RNA virus and signals required for said virus mediated replication and transcription, operatively linked to an RNA sequence, and collectively encoding the required functional transcriptional units of said RNA virus, wherein each encodes a subset of the required functional transcriptional units of said RNA virus and wherein one or more of said recombinant RNA molecules encodes a functional transcriptional unit of said RNA virus operatively linked to a heterologous RNA sequence. More particularly, the heterologous sequence or sequences may encode a viral antigen, tumor antigen or therapeutic protein. Such viral antigen may be derived from a virus selected from the group of human immunodeficiency virus, Newcastle disease virus, influenza, respiratory syncytial virus, Marek's disease virus, infectious bursal disease virus, infectious bronchitis virus, infectious bursitis virus, chicken anemia virus, infectious laryngotracheitis virus, avian leukosis virus, reticuloendotheliosis virus, avian influenza virus, rabies virus, feline distemper virus, vesicular stomatitis virus, rinderpest virus, and swinepox virus.

A further embodiment of the invention extends to a set of two or more segmented recombinant RNA molecules comprising a binding site specific for an RNA polymerase of a naturally non-segmented RNA virus and signals required for said virus mediated replication and transcription, operatively linked to an RNA sequence, and collectively encoding the required functional transcriptional units of said RNA virus, wherein each encodes a subset of the required functional transcriptional units of said RNA virus and wherein one or more of said recombinant RNA molecules contains a mutation, insertion or deletion.

Either of the aforementioned recombinant molecules may be prepared as a chimeric virus. Further, a heterologous RNA in such a chimeric virus may be derived from a viral antigen, and the viral antigen in turn, may be derived from a virus selected from the group of human immunodeficiency virus, Newcastle disease virus, influenza, respiratory syncytial virus, Marek's disease virus, infectious bursal disease virus, infectious bronchitis virus, infectious bursitis virus, chicken anemia virus, infectious laryngotracheitis virus, avian leukosis virus, reticuloendotheliosis virus, avian influenza virus, rabies virus, feline distemper virus, vesicular stomatitis virus, rinderpest virus, and swinepox virus.

The invention extends to a method for producing a chimeric naturally non-segmented negative-strand RNA virus, which comprises transfecting a host cell with nucleotide sequences encoding the set of recombinant RNA molecules just described above, and the viral functions required for replication and transcription, and recovering the chimeric virus thus produced.

The invention also extends to a vaccine formulation comprising a recombinant naturally non-segmented negative-strand RNA virus having a recombinantly segmented genome produced by this method and a pharmaceutically acceptable excipient or vehicle. The invention provides a vaccine formulation comprising a recombinant chimeric negative strand virus produced by this method, which virus encodes a heterologous epitope, and a pharmaceutically acceptable excipient or vehicle. The vaccine formulation may be prepared with the heterologous epitope comprising a pathogen antigen or cancer antigen, including but not limited to a bacterial antigen, a parasite antigen, and an oncogene or modified oncogene. The vaccine formulation may be prepared with the heterologous epitope comprising a viral antigen, and the viral antigen may be derived from a virus selected from the group of human immunodeficiency virus, Newcastle disease virus, influenza, respiratory syncytial virus, Marek's disease virus, infectious bursal disease virus, infectious bronchitis virus, infectious bursitis virus, chicken anemia virus, infectious laryngotracheitis virus, avian leukosis virus, reticuloendotheliosis virus, avian influenza virus, rabies virus, feline distemper virus, vesicular stomatitis virus, rinderpest virus, and swinepox virus. Further, the heterologous epitope may be an immunoprecipitating protein or a tumor antigen. The invention further extends to a therapeutic formulation comprising a recombinant naturally non-segmented negative-strand RNA virus having a recombinantly segmented genome produced by this method and a pharmaceutically acceptable excipient or vehicle. The invention provides a therapeutic formulation comprising a recombinant chimeric negative strand virus produced by this method, which virus encodes a heterologous polypeptide, and a pharmaceutically acceptable excipient or vehicle. The therapeutic formulation may be prepared with the heterologous polypeptide comprising oncogenes or modified oncogenes, genes encoding ligands or receptor binding proteins, genes of therapeutic proteins, and genes for growth factors or immunomodulatory molecules.

Bicistronic mRNAs can be constructed to permit internal initiation of translation of viral sequences and allow for the expression of foreign protein coding sequences from the regular terminal initiation site, or vice versa. Alternatively, a foreign protein may be expressed from an internal transcriptional unit in which the transcriptional unit has an initiation site and polyadenylation site. In another embodiment, the foreign gene is inserted into a viral gene such that the resulting expressed protein is a fusion protein.

The recombinant mutant negative-strand viral RNA templates of the present invention may be used to transfect transformed cell lines that express the RNA dependent RNA-polymerase and allow for complementation. Alternatively, a plasmid expressing from an appropriate promoter, can be used for virus specific (chimeric) RNA transfection. Complementation may also be achieved with the use of a helper virus which provides the RNA dependent RNA-polymerase.

Additionally, a non-virus dependent replication system for non-segmented negative-strand RNA virus is also described. The minimum subset of non-segmented negative-strand RNA virus proteins needed for specific replication and expression of the virus are the three proteins, L, P and NP, which can be expressed from plasmids for example by a vaccinia virus T7 system. In yet another embodiment, when plasmids encoding the antigenomic copy of the negative strand virus genome are used to supply the viral genome, the minimum subset of Newcastle disease virus proteins needed for specific replication and expression of the virus are the L and P proteins.

The expression products and/or recombinant or chimeric virions obtained may advantageously be utilized in vaccine formulations. The expression products and chimeric virions of the present invention may be engineered to create vaccines against a broad range of pathogens, including viral antigens, tumor antigens and auto antigens involved in autoimmune disorders. In a particular embodiment and by way of example, the chimeric virions of the present invention may be engineered to create anti-HIV vaccines, wherein an immunogenic polypeptide from gp160, and/or from internal proteins of HIV is engineered into a negative strand virus protein, for instance the glycoprotein HN protein, to construct a vaccine that is able to elicit both vertebrate humoral and cell-mediated immune responses. The use of recombinant Newcastle disease virus for this purpose is especially attractive since Newcastle disease virus is not pathogenic in humans. Furthermore, as Newcastle disease virus and various other negative strand viruses (including but not limited to VSV, avian and bovine RSV) are not natural pathogens of humans, humans will not have pre-existing antibodies to these viruses, and can mount a significant response, being naive to the antigens, on vaccination using these viruses in vaccine formulation. Additionally, the use of for example recombinant Newcastle disease virus for delivering tumor antigens is particularly attractive given the known antineoplastic and immunopotentiating properties of the virus.

The system and method of the present invention possesses particular advantages, among them that virus replication and transcription may be achieved at higher rates and efficiency, as the use of plural genomic segments proceeds with greater speed and facility. Also, the use of plural genomic segments permits greater latitude in the insertion and packaging of foreign inserts and potentiates the expression of the latter, and yet further, confers an added measure of safety in the corresponding increase in attenuation that results from segmentation. Lastly, the system has as one of its characteristics and advantages that the recombinant virus may be prepared and assembled as a single particle. This avoids the need for complementation and yields corresponding efficiencies in the use of the resulting recombinant virus.

DEFINITIONS

As used herein, the following terms will have the meanings indicated:

cRNA=anti-genomic RNA

HIV=human immunodeficiency virus

L=large protein

M=matrix protein (lines inside of envelope)

moi=multiplicity of infection

NA=neuraminidase (envelope glycoprotein)

NDV=Newcastle disease Virus

NP=nucleoprotein (associated with RNA and required for polymerase activity)

NS=nonstructural protein (function unknown)

nt=nucleotide

PA, PB1, PB2=RNA-directed RNA polymerase components
RNP=ribonucleoprotein
rRNP=recombinant RNP
vRNA=genomic virus RNA

DESCRIPTION OF THE FIGURES

FIG. 1. Generation of recombinant segmented viruses for negative-strand naturally non-segmented viruses. A system for NDV is described as an example. Two biologically active viral ribonucleoproteins (RNP) are generated inside transfected cells. One of the RNPs contains a subset of the six functional transcriptional units of NDV. The second RNP contains the functional transcriptional units which are not present in the first RNP. To reconstitute the RNPs, the required viral nucleoprotein (N) and RNA polymerase proteins (L and P) can be expressed by different methods, including transfecting T7-responsive plasmids into cells that have been infected with a vaccinia virus vector expressing T7 polymerase, and stable expression of these proteins in complementing cell lines. The two viral RNA segments are expressed by transfecting T7-responsive plasmids or naked RNAs. The two segments can be expressed in negative or in positive polarity. Both RNAs are flanked by NDV-specific promoters located at their 3' and 5' ends. The intracellularly assembled RNPs are transcribed and replicated by the viral RNA polymerase, leading to the formation of infectious viruses. Both RNPs are required for infectivity, since only viruses containing the two will encode all functional genes required for viral production.

DESCRIPTION OF THE INVENTION

This invention relates to genetically engineered negative-strand non-segmented RNA viruses and viral vectors which are generated from one or more biologically active viral ribonucleoproteins (RNP). The invention relates to negative-strand RNA viruses and viral templates for naturally non-segmented RNA viruses which are generated using the methods of the present invention from two or more recombinant RNA molecules or recombinant segments.

The invention further relates to recombinant negative strand viruses and viral templates that express heterologous genes or mutated homologous negative strand viral genes or a combination of viral genes derived from different strains of the negative strand RNA virus. The invention relates to the construction and use of segmented recombinant negative strand viral RNA templates or molecules which may be used with viral RNA-directed RNA polymerase to express heterologous gene products in appropriate host cells and/or to rescue the heterologous gene in virus particles. In one embodiment of the invention, the heterologous gene product is a peptide or protein derived from the genome of a human immunodeficiency virus. The RNA templates of the present invention may be prepared either in vitro or in vivo by transcription of appropriate DNA sequences using an appropriate and effective polymerase, including for example a DNA-directed RNA polymerase such as bacteriophage T7, T3, the SP6 polymerase or an appropriate eukaryotic polymerase such as polymerase I. The skilled artisan can readily assess or determine those polymerases appropriate or effective for use in preparing RNA molecules or RNA templates in accordance with the present invention.

The recombinant RNA templates or molecules may be used to transfect continuous/transfected cell lines that express the RNA-directed RNA polymerase proteins allowing for complementation. In a preferred embodiment, a non-virus dependent replication system is used to recover chimeric negative strand virus, in which plasmid DNA encoding the negative strand genome or antigenome one two or more segments is coexpressed with plasmid DNA encoding the minimum subset of negative-strand virus proteins needed for specific replication and expression of the virus, as demonstrated by way of working example as described herein.

The ability to recombinantly reconstitute negative strand virus in vivo allows the design of novel chimeric negative strand viruses which express foreign genes or which express mutant viral genes. The ability to reconstitute negative-strand virus in vivo also allows the design of novel chimeric viruses which express genes from different strains or variants of a particular negative-strand virus. One way to achieve this goal involves modifying existing viral genes. For example, the HN gene may be modified to contain foreign sequences in its external domains. Where the heterologous sequence are epitopes or antigens of pathogens, these chimeric viruses may be used to induce a protective immune response against the disease agent from which these determinants are derived.

In accordance with one embodiment of the present invention, two or more RNA segments or RNPs are generated, one of which comprises a chimeric RNA in which a coding sequence derived from human immunodeficiency virus, for instance the gp160 coding region, is inserted into the HN coding sequence of negative strand RNA virus NDV, and chimeric recombinant virus is produced by transfection of this chimeric RNA segment, along with the other viral RNA segment(s) and with T7-responsive plasmids expressing the required viral nucleoprotein (N) and RNA polymerase proteins (L and P), into a host cell expressing T7 polymerase. Further, such a chimeric virus should be capable of eliciting both a vertebrate humoral and cell-mediated immune response.

The present invention further relates to the design of novel chimeric negative strand viruses which have altered or expanded tropism, for example by virtue of expression of receptor binding proteins for instance for recognition of and permissive infection of human cells, or for example by virtue of altered tropism for recognition, binding to or infection of particular cells, cell types or tissues. The ability to reconstitute negative-strand virus in vivo also allows the design of novel chimeric viruses with altered, specific or enhanced tropism. One way to achieve this goal involves modifying existing viral genes. For example, the receptor binding protein may be modified to recognize or bind to human cells or to do so more effectively or efficiently. For instance, in the case of NDV the HN hemagglutinin protein, which is the receptor binding protein, may be altered or replaced such that human cells will be recognized and infected more effectively/efficiently. The receptor binding protein of other naturally non-segmented negative strand viruses may be similarly altered or replaced, including for instance, the H protein in measles virus, the G protein in VSV, RSV or rhabdovirus, and the F protein in RSV. In a further embodiment, the virus may be altered or may express a heterologous gene which will make the virus more selective for a particular tissue or target specific cells. For example, in targeting a negative strand virus to cancer cells, they may be engineered to recognize or bind to a receptor protein or surface protein expressed on cancer cells, e.g. the Fc receptor.

The present invention relates to the use of viral vectors and chimeric viruses of the invention to formulate vaccines against a broad range of viruses and/or antigens including tumor antigens. The viral vectors and chimeric viruses of the present invention may be used to modulate a subject's immune system by stimulating a humoral immune response, a cellular immune response or by stimulating tolerance to an antigen. As used herein, a subject means: humans, primates, horses, cows, sheep, pigs, goats, dogs, cats, avian species and rodents. When delivering, tumor antigens, the invention may be used to treat subjects having disease amenable to immunity mediated rejection, such as non-solid tumors or solid tumors of small size. It is also contemplated that delivery of tumor antigens by the viral vectors and chimeric viruses described herein will be useful for treatment subsequent to removal of large solid tumors. The invention may also be used to treat subjects who are suspected of having cancer.

Construction of Recombinant Heterologous RNA Templates

Heterologous gene coding sequences flanked by the complement of the viral polymerase binding site/promoter, e.g., the complement of 3'-NDV virus terminus of the present invention, or the complements of both the 3'- and 5'-NDV virus termini may be constructed using techniques known in the art. The resulting RNA templates may be of the negative-polarity and contain appropriate terminal sequences which enable the viral RNA-synthesizing apparatus to recognize the template. Alternatively, positive-polarity RNA templates which contain appropriate terminal sequences which enable the viral RNA-synthesizing apparatus to recognize the template, may also be used. Recombinant DNA molecules containing these hybrid sequences can be cloned and transcribed by a DNA-directed RNA polymerase, such as bacteriophage T7, T3, the SP6 polymerase or eukaryotic polymerase such as polymerase I and the like, to produce in vitro or in vivo the recombinant RNA molecules which possess the appropriate viral sequences that allow for viral polymerase recognition and activity.

In yet another embodiment, virtually any heterologous sequence, including one or more heterologous sequence, may be constructed into the chimeric viruses of the present invention. The heterologous sequence or sequences include but are not limited to antigens, such as 1) antigens that are characteristic of a pathogen; 2) antigens that are characteristic of autoimmune disease; 3) antigens that are characteristic of an allergen; and 4) antigens that are characteristic of a tumor. For example, heterologous gene sequences that can be engineered into the chimeric viruses of the invention include, but are not limited to, epitopes of human immunodeficiency virus (HIV) such as gp160; hepatitis B virus surface antigen (HBsAg); the glycoproteins of herpes virus (e.g., gD, gE); VP1 of poliovirus; and antigenic determinants of nonviral pathogens such as bacteria and parasites to name but a few.

Antigens that are characteristic of autoimmune disease typically will be derived from the cell surface, cytoplasm, nucleus, mitochondria and the like of mammalian tissues, including antigens characteristic of diabetes mellitus, multiple sclerosis, systemic lupus erythematosus, rheumatoid arthritis, pernicious anemia, Addison's disease, scleroderma, autoimmune atrophic gastritis, juvenile diabetes, and discoid lupus erythematosus.

Antigens that are allergens are generally proteins or glycoproteins, including antigens derived from pollens, dust, molds, spores, dander, insects and foods.

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and glycoproteins. Tumors include, but are not limited to, those derived from the types of cancer: lip, nasopharynx, pharynx and oral cavity, esophagus, stomach, colon, rectum, liver, gall bladder, pancreas, larynx, lung and bronchus, melanoma of skin, breast, cervix, uterine, ovary, bladder, kidney, uterus, brain and other parts of the nervous system, thyroid, prostate, testes, Hodgkin's disease, non-Hodgkin's lymphoma, multiple myeloma and leukemia.

In one specific embodiment of the invention, the heterologous sequences are derived from the genome of human immunodeficiency virus (HIV), preferably human immunodeficiency virus-1 or human immunodeficiency virus-2. In another embodiment of the invention, the heterologous coding sequences may be inserted within a viral gene coding sequence such that a chimeric gene product is expressed which contains the heterologous peptide sequence within the viral protein. In such an embodiment of the invention, the heterologous sequences may also be derived from the genome of a human immunodeficiency virus, preferably of human immunodeficiency virus-1 or human immunodeficiency virus-2.

In instances whereby the heterologous sequences are HIV-derived, such sequences may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25) tat, rev, nef, vif, vpu, vpr, and/or vpx.

In a further embodiment, heterologous gene sequences that can be engineered into the chimeric viruses include, but are not limited to, oncogenes or modified oncogenes (e.g. dominant negative oncogenes), genes encoding ligands or receptor binding proteins, genes of therapeutic proteins, and genes for growth factors or immunomodulatory molecules. In yet another embodiment, heterologous gene sequences that can be engineered into the chimeric viruses include those that encode proteins with immunopotentiating activities. Examples of immunopotentiating proteins include, but are not limited to, cytokines, interferon type 1, gamma interferon, colony stimulating factors, interleukin-1, -2, -4, -5, -6, -12. The heterologous gene sequences may be the natural gene sequences of the desired polypeptide or may be modified by sequence mutation, insertion or deletion. Such modified heterologous sequences may be altered to provide a novel phenotype or characteristic (for instance enhanced enzymatic activity), to include an antigenic site, to include a ligand binding site, to add an additional enzymatic capacity or other function, or be altered in sequence to be more efficiently expressed in the chimeric viral system (for instance taking into account codon usage or preference of the virus).

One approach for constructing these hybrid molecules is to insert the heterologous coding sequence into a DNA complement of a viral gene of a naturally non-segmented negative strand virus so that the heterologous sequence is flanked by the viral sequences required for viral polymerase activity; i.e., the viral polymerase binding site/promoter, hereinafter referred to as the viral polymerase binding site, and a polyadenylation site. In a preferred embodiment, the heterologous coding sequence is flanked by the viral sequences that comprise the replication promoters of the 5' and 3' termini, the gene start and gene end sequences, and the packaging signals that are found in the 5' and/or the 3' termini. In an alternative approach, oligonucleotides encoding the viral polymerase binding site, e.g., the complement of the 3'-terminus or both termini of the virus genomic segments can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82; 488). Variations in polymerase chain reaction (PCR) technology, described infra, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophage T3, T7 or SP6) and the hybrid sequence containing the heterologous gene and the NDV polymerase binding site. RNA templates could then be transcribed directly from this recombinant DNA. In yet another embodiment, the recombinant RNA templates may be prepared by ligating RNAs specifying the negative polarity of the heterologous gene and the viral polymerase binding site using an RNA ligase. Sequence requirements for viral polymerase activity and constructs which may be used in accordance with the invention are described in the subsections below.

Insertion of the Heterologous Gene Sequence into the Viral HN, P, NP, M, F, L Genes In an embodiment of the present invention, the gene segments coding for the HN, P, NP, M, F, or L proteins may be used for the insertion of heterologous gene products. Insertion of a foreign gene sequence into any of these segments could be accomplished by either a complete replacement of the viral coding region with the foreign gene or by a partial replacement. Complete replacement would probably best be accomplished through the use of PCR-directed mutagenesis. Briefly, PCR-primer A would contain, from the 5' to 3' end: a unique restriction enzyme site, such as a class IIS restriction enzyme site (i.e., a "shifter" enzyme; that recognizes a specific sequence but cleaves the DNA either upstream or downstream of that sequence); a stretch of nucleotides complementary to a region of the particular viral gene; and a stretch of nucleotides complementary to the carboxy-terminus coding portion of the foreign gene product. PCR-primer B would contain from the 5' to 3' end: a unique restriction enzyme site; a stretch of nucleotides complementary to a particular viral gene; and a stretch of nucleotides corresponding to the 5' coding portion of the foreign gene. After a PCR reaction using these primers with a cloned copy of the foreign gene, the product may be excised and cloned using the unique restriction sites. Digestion with the class IIS enzyme and transcription with the purified phage polymerase would generate an RNA molecule containing the exact untranslated ends of the particular viral gene with a foreign gene insertion. In an alternate embodiment, PCR-primed reactions could be used to prepare double-stranded DNA containing the bacteriophage promoter sequence, and the hybrid gene sequence so that RNA templates can be transcribed directly without cloning.

Insertion of the Heterologous Gene Sequence into the HN Gene

The hemagglutinin and neuraminidase activities of NDV are coded for by a single gene, HN. The HN protein is a major surface glycoprotein of the virus. For a variety of viruses, such as influenza, the hemagglutinin and neuraminidase proteins have been demonstrated to contain a number of antigenic sites. Consequently, this protein is a potential target for the humoral immune response after infection. Therefore, substitution of antigenic sites within HN with a portion of a foreign protein may provide for a vigorous humoral response against this foreign peptide. If a sequence is inserted within the HN molecule and it is expressed on the outside surface of the HN it will be immunogenic. For example, a peptide derived from gp160 of HIV could replace an antigenic site of the HN protein, resulting in the elicitation of both a cellular and humoral immune response. In a different approach, the foreign peptide sequence may be inserted within the antigenic site without deleting any viral sequences. Expression products of such constructs may be useful in vaccines against the foreign antigen, and may indeed circumvent a problem discussed earlier, that of propagation of the recombinant virus in the vaccinated host. An intact HN molecule with a substitution only in antigenic sites may allow for HN function and thus allow for the construction of a viable virus. Therefore, this virus can be grown without the need for additional helper functions. The virus may also be attenuated in other ways to avoid any danger of accidental escape. Other hybrid constructions may be made to express proteins on the cell surface or enable them to be released from the cell. As a surface glycoprotein, the HN has an amino-terminal cleavable signal sequence necessary for transport to the cell surface, and a carboxy-terminal sequence necessary for membrane anchoring. In order to express an intact foreign protein on the cell surface it may be necessary to use these HN signals to create a hybrid protein. In this case, the fusion protein may be expressed as a separate fusion protein from an additional internal promoter. Alternatively, if only the transport signals are present and the membrane anchoring domain is absent, the protein may be secreted out of the cell.

Construction of Bicistronic RNA and Heterologous Protein Expression

Bicistronic mRNA could be constructed to permit internal initiation of translation of viral sequences and allow for the expression of foreign protein coding sequences from the regular terminal initiation site. Alternatively, a bicistronic mRNA sequence may be constructed wherein the viral sequence is translated from the regular terminal open reading frame, while the foreign sequence is initiated from an internal site. Certain internal ribosome entry site (IRES) sequences may be utilized. The IRES sequences which are chosen should be short enough to not interfere with virus packaging limitations. Thus, it is preferable that the IRES chosen for such a bicistronic approach be no more than 500 nucleotides in length, with less than 250 nucleotides being preferred. Further, it is preferable that the IRES utilized not share sequence or structural homology with picornaviral elements. Preferred IRES elements include, but are not limited to the mammalian BiP IRES and the hepatitis C virus IRES.

Alternatively, a foreign protein may be expressed from a new internal transcriptional unit in which the transcriptional unit has an initiation site and polyadenylation site. In another embodiment, the foreign gene is inserted into a naturally non-segmented negative strand virus gene such that the resulting expressed protein is a fusion protein.

Expression of Heterologous Gene Products using Recombinant RNA Template

The recombinant templates prepared as described above can be used in a variety of ways to express the heterologous gene products in appropriate host cells or to create chimeric viruses that express the heterologous gene products. In one embodiment, the recombinant template can be used to transfect appropriate host cells, may direct the expression of the heterologous gene product at high levels. Host cell systems which provide for high levels of expression include continuous cell lines that supply viral functions such as cell lines superinfected with NDV, cell lines engineered to complement NDV functions, etc.

In an alternate embodiment of the invention, the recombinant templates may be used to transfect cell lines that express a viral polymerase protein in order to achieve expression of the heterologous gene product. To this end, transformed cell lines that express a polymerase protein such as the L protein may be utilized as appropriate host cells. Host cells may be similarly engineered to provide other viral functions or additional functions such as NP or HN.

In another embodiment, a helper virus may provide the RNA polymerase protein utilized by the cells in order to achieve expression of the heterologous gene product.

In yet another preferred embodiment, cells may be transfected with vectors encoding the NP, P and L viral proteins. The required viral nucleoprotein (N) and RNA polymerase proteins (L and P) can be expressed by different methods, including transfecting T7-responsive plasmids into cells that have been infected with a vaccinia virus vector expressing T7 polymerase, and stable expression of these proteins in complementing cell lines.

Preparation of Chimeric Negative Strand RNA Virus

In order to prepare chimeric virus, recombinant negative strand virus RNAs coding for the negative strand virus genome and/or foreign proteins in the plus or minus sense in two or more segments or RNAs may be used to transfect cells which provide viral proteins and functions required for replication and rescue or are also infected with a "parent" virus. In an alternative approach, plasmids encoding the genomic or antigenomic viral RNA in two or more segments, either wild type or modified, may be co-transfected into host cells with plasmids encoding viral polymerase proteins, e.g., NP, P or L. In another embodiment, plasmids encoding the antigenomic viral RNA in two or more segments may be co-transfected with plasmids encoding viral polymerase proteins P and L, as the NP polymerase protein is the first protein transcribed by the antigenomic copy of the NDV genome for instance, it is not necessary to additionally provide the NP polymerase in trans.

In an embodiment of the present invention, the recombinant method of the present invention may be utilized to engineer the chimeric negative strand RNA virus, this technique involves the preparation of synthetic recombinant viral RNAs that contain the non-coding regions of the negative strand virus RNA which are essential for the recognition by viral polymerases and for packaging signals necessary to generate a mature virion. The synthetic recombinant plasmid DNAs and RNAs can be replicated and rescued into infectious virus particles by any number of techniques known in the art, as described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

There are a number of different approaches which may be used to apply the reverse genetics approach to rescue negative strand RNA viruses. First, the recombinant RNAs are synthesized from a recombinant DNA template and reconstituted in vitro with purified viral polymerase complex to form recombinant ribonucleoproteins (RNPs) which can be used to transfect cells. In another approach, a more efficient transfection is achieved if the viral polymerase proteins are present during transcription of the synthetic RNAs either in vitro or in vivo. With this approach the synthetic RNAs may be transcribed from cDNA plasmids which are either co-transcribed in vitro with cDNA plasmids encoding the polymerase proteins, or transcribed in vivo in the presence of polymerase proteins, i.e., in cells which transiently or constitutively express the polymerase proteins.

In an alternate embodiment, a combination of reverse genetics techniques and reassortant techniques can be used to engineer attenuated viruses having the desired epitopes in segmented RNA viruses. For example, an attenuated virus (generated by natural selection, mutagenesis or by reverse genetics techniques) and a strain carrying the desired vaccine epitope (generated by natural selection, mutagenesis or by reverse genetics techniques) can be co-infected in hosts that permit reassortment of the segmented genomes. Reassortants that display both the attenuated phenotype and the desired epitope can then be selected.

Following reassortment, the novel viruses may be isolated and their genomes identified through hybridization analysis. In additional approaches described herein, the production of infectious chimeric virus may be replicated in host cell systems that express an NDV viral polymerase protein (e.g., in virus/host cell expression systems; transformed cell lines engineered to express a polymerase protein, etc.), so that infectious chimeric virus are rescued. In this instance, helper virus need not be utilized since this function is provided by the viral polymerase proteins expressed.

In accordance with the present invention, any technique known to those of skill in the art may be used to achieve replication and rescue of chimeric viruses. One approach involves supplying viral proteins and functions required for replication in vitro prior to transfecting host cells. In such an embodiment, viral proteins may be supplied in the form of wildtype virus, helper virus, purified viral proteins or recombinantly expressed viral proteins. The viral proteins may be supplied prior to, during or post transcription of the synthetic cDNAs or RNAs encoding the chimeric virus. The entire mixture may be used to transfect host cells. In another approach, viral proteins and functions required for replication may be supplied prior to or during transcription of the synthetic cDNAs or RNAs encoding the chimeric virus. In such an embodiment, viral proteins and functions required for replication are supplied in the form of wildtype virus, helper virus, viral extracts, synthetic cDNAs or RNAs which express the viral proteins are introduced into the host cell via infection or transfection. This infection/transfection takes place prior to or simultaneous to the introduction of the synthetic cDNAs or RNAs encoding the chimeric virus.

In a particularly desirable approach, cells engineered to express all viral genes for a naturally non-segmented negative-strand virus from two or more RNA molecules or segments may result in the production of infectious recombinant or chimeric virus which contain the desired genotype; thus eliminating the need for a selection system or any helper virus. Theoretically, one can replace any one of the six genes or part of any one of the six genes of virus with a foreign sequence. However, a necessary part of this equation is the ability to propagate the defective virus (defective because a normal viral gene product is missing or altered). A number of possible approaches exist to circumvent this problem. In one approach a virus having a mutant protein can be grown in cell lines which are constructed to constitutively express the wild type version of the same protein. By this way, the cell line complements the mutation in the virus. These cell lines which are made to express the viral protein may be used to complement the defect in the recombinant virus and thereby propagate it. Certain natural host range systems may be available to propagate recombinant virus.

Alternatively, and in as much as by virtue of the present invention, the negative strand viruses are being generated from two or more segments or RNA molecules, the foreign sequence may be used or expressed as a fusion protein with a viral protein or as an additional protein, additional to the required viral proteins, particularly if the length or size of the viral protein does not interfere with viral packaging.

As stated earlier, the use of segmented vectors for naturally non-segmented negative strand viruses as set forth herein, has certain advantages over the use of conventional non-segmented vectors. First, since the genome is divided into two or more segments, each of these segments can be smaller than the wild-type non-segmented genome. It is predicted that smaller RNA segments will have higher replication and transcriptional rates, and that they will accommodate longer insertions encoding foreign sequences. Thus, segmented vectors expressing foreign antigens will be more versatile and will express their foreign inserts to higher levels than non-segmented vectors. Second, the segmentation of the genome of a naturally non-segmented virus is most likely attenuating the virus, adding an extra safety measure to the use of segmented vectors for vaccines in animals or humans. Recombinant segmented vectors expressing one or more foreign antigens, heterologous proteins and/or immunostimulatory molecules could be used as effective vaccines or therapies against different diseases, including AIDS and cancer.

Vaccine and Therapeutic Formulations using the Chimeric Viruses

The invention encompasses vaccine formulations and therapeutic formulations comprising the engineered negative strand RNA virus of the present invention. The invention encompasses the use of recombinant naturally non-segmented negative-strand viruses which have been modified in vaccine formulations to confer protection against virus infection or to facilitate or initiate immune response to cancer antigens. In yet another embodiment, the recombinant naturally non-segmented negative-strand viruses of the present invention may be used as a vehicle to express foreign epitopes that induce a protective response to any of a variety of pathogens. In a further embodiment, the recombinant viruses of the present invention may be used as a vehicle to express heterologous polypeptides or therapeutic proteins, including but not limited to oncogenes or modified oncogenes, ligands or receptor binding proteins, and growth factors or immunomodulatory molecules.

The invention encompasses vaccine formulations and therapeutic formulations to be administered to humans and animals. In particular, the invention encompasses vaccine formulations and therapeutic formulations to be administered to domestic animals, including dogs and cats; wild animals, including foxes and racoons; and livestock, including cattle, horses, and pigs, sheep and goats; and fowl, including chicken and turkey.

The invention encompasses vaccine formulations which are useful against avian disease causing agents including NDV, Marek's Disease Virus (MDV), Infectious Bursal Disease Virus (IBDV), Infectious Bronchitis Virus (BIV), Infectious Bursitis Virus, Chicken Anemia Virus (CAV), Infectious Laryngotracheitis Virus (ILV), Avian Leukosis Virus (ALV), Reticuloendotheliosis Virus (RV) and Avian Influenza Virus.

In another embodiment, the invention encompasses vaccine formulations which are useful against domestic disease causing agents including rabies virus, feline leukemia virus (FLV) and canine distemper virus. In yet another embodiment, the invention encompasses vaccine formulations which are useful to protect livestock against vesicular stomatitis virus, rabies virus, rinderpest virus, swinepox virus, and further, to protect wild animals against rabies virus.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain. For example, antigens of non-related viruses such as HIV (gp160, gp120, gp41) parasite antigens (e.g., malaria), bacterial or fungal antigens or tumor antigens can be engineered into the attenuated strain. Alternatively, epitopes which alter the tropism of the virus in vivo can be engineered into the chimeric attenuated viruses of the invention.

Virtually any heterologous gene sequence may be constructed into the chimeric viruses of the invention for use in vaccines. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention include, but are not limited to influenza glycoproteins, in particular, hemagglutinin H5, H7, Marek's Disease Viral epitopes; epitopes of Infectious Bursal Disease Virus (IBDV), Infectious Bronchitis Virus (IBV), Chicken Anemia Virus (CAV), Infectious Laryngotracheitis Virus (ILV), Avian Leukosis Virus (ALV), Reticuloendotheliosis Virus (RV), Avian Influenza Virus (AIV), rabies virus, feline leukemia virus, canine distemper virus, vesicular stomatitis virus, rinderpest virus, and swinepox virus (see Fields et al. (ed.), 2001, *Fundamental Virology, Fourth Edition*, Raven Press, New York, incorporated by reference herein in its entirety).

In yet another embodiment, heterologous gene sequences that can be engineered into the chimeric viruses include those that encode proteins with immunopotentiating activities. Examples of immunopotentiating proteins include, but are not limited to, cytokines, interferon type 1, gamma interferon, colony stimulating factors, interleukin-1, -2, -4, -5, -6, -12.

In addition, heterologous gene sequences that can be constructed into the chimeric viruses of the invention for use in vaccines include but are not limited to sequences derived from a human immunodeficiency virus (HIV), preferably type 1 or type 2. In a preferred embodiment, an immunogenic HIV-derived peptide which may be the source of an antigen may be constructed into a chimeric NDV that may then be used to elicit a vertebrate immune response. Such HIV-derived peptides may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25), tat, rev, nef, vif, vpu, vpr, and/or vpx.

Other heterologous sequences may be derived from hepatitis B virus surface antigen (HBsAg); hepatitis A or C virus surface antigens, the glycoproteins of Epstein Barr virus; the glycoproteins of human papillomavirus; the glycoproteins of respiratory syncytial virus, parainfluenza virus, Sendai virus, simian virus 5 or mumps virus; the glycoproteins of influenza virus; the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Other heterologous sequences may be derived from tumor antigens, and the resulting chimeric viruses be used to generate an immune response against the tumor cells leading to tumor regression in vivo. These vaccines may be used in combination with other therapeutic regimens, including but not limited to chemotherapy, radiation therapy, surgery, bone marrow transplantation, etc. for the treatment of tumors. In accordance with the present invention, recombinant viruses may be engineered to express tumor-associated antigens (TAAs), including but not limited to, human tumor antigens recognized by T cells (Robbins and Kawakami, 1996, Curr. Opin. Immunol. 8:628-636, incorporated herein by reference in its entirety), melanocyte lineage proteins, including gp100, MART-1/MelanA, TRP-1 (gp75), tyrosinase; Tumor-specific widely shared antigens, MAGE-1, MAGE-3, BAGE, GAGE-1, GAGE-1, N-acetylglucosaminyltransferase-V, p15; Tumor-specific mutated antigens, β-catenin, MUM-1, CDK4; Nonmelanoma antigens for breast, ovarian, cervical and pancreatic carcinoma, HER-2/neu, human papillomavirus-E6, -E7, MUC-1.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification. Additionally, as NDV has been demonstrated to be non-pathogenic in humans, this virus is highly suited for use as a live vaccine.

In this regard, the use of genetically engineered negative-strand virus (vectors) for vaccine purposes may desire the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed. Such viruses would go through only one or a few rounds of replication within the host. When used as a vaccine, the recombinant virus would go through limited replication cycle(s) and induce a sufficient level of immune response but it would not go further in the human host and cause disease. Recombinant viruses lacking one or more of the viral genes or possessing mutated viral genes would not be able to undergo successive rounds of replication. Defective viruses can be produced in cell lines which permanently express such a gene(s). Viruses lacking an essential gene(s) will be replicated in these cell lines but when administered to the human host will not be able to complete a round of replication. Such preparations may transcribe and translate— in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and *Corynebacterium parvum*.

Many methods may be used to introduce the vaccine formulations described above, these include but are not limited to oral, intradermal, intramuscular, intraperitoneal, intravenous, subcutaneous, and intranasal routes. It may be preferable to introduce the chimeric virus vaccine formulation via the natural route of infection of the pathogen for which the vaccine is designed.

EXAMPLE

Expression and Packaging of Recombinant Non-Segmented Negative Strand RNA Virus from more than One RNA Segment Vaccination is a powerful means to prevent or treat different diseases. Although effective vaccines have been developed against a variety of infectious agents in humans and animals, there are many microbial pathogens, including HIV, for which no vaccine is available. The present example concerns a new negative-strand RNA viral vector which may be important for the development of effective vaccines against a variety of pathogens as well as against cancer. In this example, a naturally non-segmented negative-strand virus is generated recombinantly from two or more segments or from two or more RNA molecules or viral RNPS.

As one example of a naturally non-segmented negative-strand RNA virus, of the family Paramyxoviridae, an NDV vector as described here induces in humans and animals a potent B and T cell response against foreign antigens. For example, it is believed that a protective vaccine against HIV-1 infection should induce high levels of cellular and humoral immune responses against conserved HIV-1 epitopes. The identification of a safe and highly immunogenic vector expressing HIV-1 antigens is an important step towards the development of an AIDS vaccine. We believe that recombinant negative strand virus, including NDV, represents an ideal vector for such a purpose.

In addition, the genomic structure of the virus of the virus has been modified to increase its safety profile as well as its coding potential. NDV is a naturally non-segmented RNA virus. The methods described below allow the construction of naturally non-segmented RNA virus vectors, including NDV vectors, with a profound change in their genomic organization. These vectors are based on the use of recombinant NDVs containing a segmented RNA genome.

Newcastle disease virus (NDV) is a negative strand RNA virus which belongs to the genus *Rubulavirus* of the family Paramyxoviridae, of the order of the Mononegavirales. This virus is an avian pathogen and several NDV strains have been isolated which are characterized by different levels of virulence in birds. Virulent (velogenic) strains of NDV cause a highly pathogenic disease in poultry. However, avirulent (mesogenic and lentogenic) strains of NDV cause mild or asymptomatic infections and they are currently used as live vaccines in domestic poultry against Newcastle disease. Humans are not the usual hosts for NDV, but the virus has been administered to humans and been found to be safe.

The molecular organization of the NDV genome is similar to that of other parainfluenza viruses. The negative-strand RNA virus genome contains one leader sequence at the 3' end followed by six transcriptional units in the order: 3'-NP-P/V-M-F-HN-L-5'. Sequences at the end of the genome are involved in transcription and replication of the RNA by the viral RNA-dependent RNA polymerase. In addition, intergenic junctions contain gene-end, polyadenylation and gene-start signals.

Reverse genetics systems which allows the genetic manipulation of the NDV genome have been described (Peeters B P et al. (1999) J Virol 73: 5001-5009; Romer-Oberdorfer A et al. (1999) J Gen Virol 80: 2987-2995; Krishnamurthy S et al. (2000) Virology 278: 168-182; Nakaya T et al. (2001) J Virol 75: 11868-11873). However, these methods are based on generating the naturally non-segmented genome of the negative strand virus, in these cases NDV, from a single plasmid or single RNP, and methods are not described that allow or utilize a change of the basic non-segmented nature of the genome of the NDV.

Figure 1:
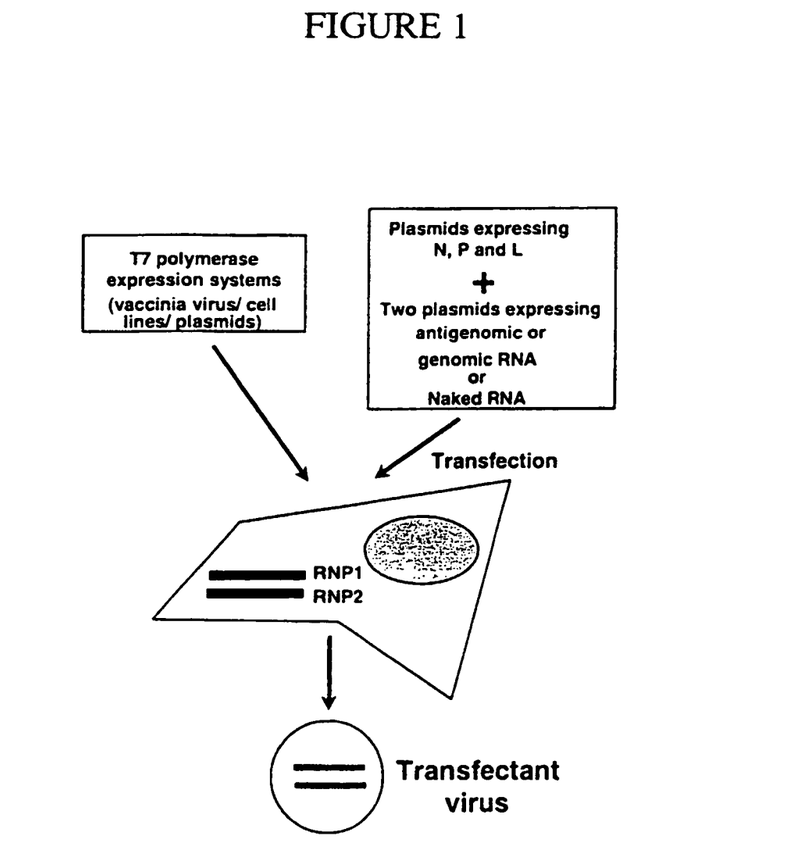

We have developed a method, depicted in FIG. 1, that allows the rescue of a recombinant naturally non-segmented negative strand RNA virus, including NDV, containing a segmented genome. This method is based on the transfection of plasmids expressing the NDV antigenome divided in two or more segments, together with plasmids expressing NP, P and L proteins of NDV.

In this method, two biologically active viral ribonucleoproteins (RNP) are generated inside transfected cells. One of the RNPs contains a subset of the six functional transcriptional units of NDV (i.e. a subset of the viral proteins NP, P/V, M, F, HN and L). The second RNP contains the functional transcriptional units which are not present in the first RNP. To reconstitute the RNPs, the required viral nucleoprotein (N) and RNA polymerase proteins (L and P) can be expressed by different methods, including transfecting T7-responsive plasmids into cells that have been infected with a vaccinia virus vector expressing T7 polymerase, and stable expression of these proteins in complementing cell lines. The two viral RNA segments are expressed by transfecting T7-responsive plasmids or naked RNAs. The two segments can be expressed in negative or in positive polarity. Both RNAs are flanked by NDV-specific promoters located at their 3' and 5' ends. The intracellularly assembled RNPs are transcribed and replicated by the viral RNA polymerase, leading to the formation of infectious viruses. Both RNPs are required for infectivity, since only viruses containing the two will encode all functional genes required for viral production.

The method depicted in FIG. 1 can be applied not only to NDV, but also to all other Mononegavirales. In addition, by dividing the six transcriptional units of the negative strand virus into more than two segments, recombinant viruses containing three or more RNA segments can be generated.

Figure 2:
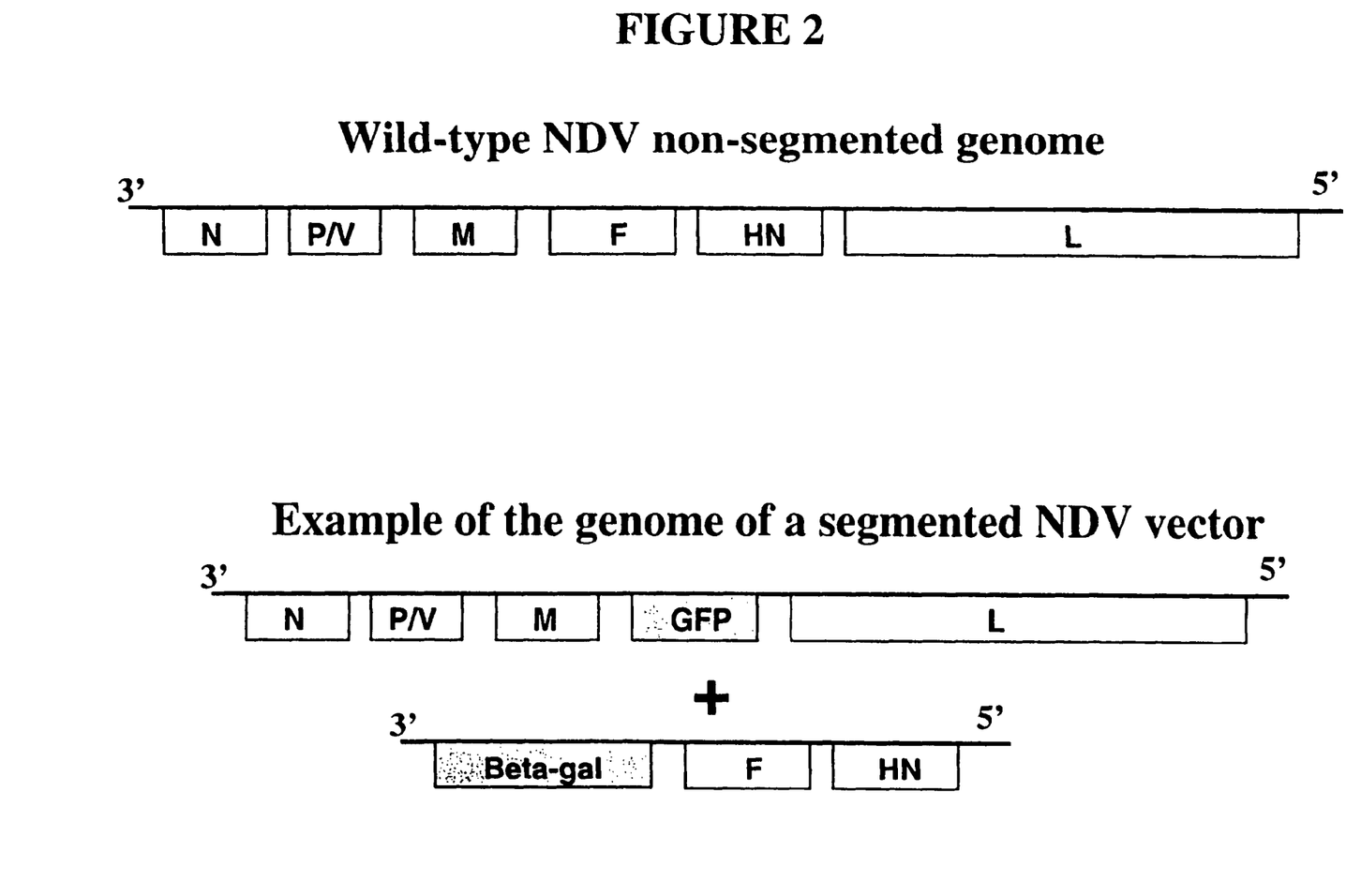
FIG. 2. Diagram of the wild type NDV non-segmented genome and of an example of the genome of a segmented NDV vector in accordance with the present invention. The N, P/V, M and L proteins are encoded from one RNP and the F and HN proteins are encoded from a second RNP or RNA segment. Marker genes for GFP and beta-gal are also encoded by the first and second RNPs respectively to enable relative assessment of RNAs, expression levels and efficiency of packaging in NDV particles.

An example of one approach to segmented RNA molecules for NDV virus is depicted in FIG. 2. FIG. 2 shows a diagram of the wild type NDV non-segmented genome and of an example of the genome of a segmented NDV vector in accordance with the present invention. The N, P/V, M and L proteins are encoded from one RNP as well as the marker gene GFP. The F and HN proteins are encoded from a second RNP or RNA segment as well as the marker gene Beta-gal. The presence of distinct marker genes on each RNP enables relative assessment of RNAs, expression levels and efficiency of packaging in NDV particles.

The use of segmented vectors for naturally non-segmented negative-strand RNA viruses, including NDV vectors, is expected to have some advantages over the use of conventional non-segmented negative strand virus vectors (i.e. where a single segment or RNA encoding all viral proteins is utilized in a recombinant system). First, since the genome is divided into two or more segments, each of these segments can be smaller than the wild-type non-segmented genome. It is predicted that smaller RNA segments will have higher replication and transcriptional rates, thus more efficiently generating recombinant virus (Kolakofsky, D. (1976) Cell 8:547-555). In addition, due to the smaller size of the RNA segments, they will accommodate longer insertions encoding foreign sequences. Thus, segmented vectors for naturally non-segmented negative strand viruses expressing foreign antigens will be more versatile and will express their foreign inserts to higher levels than non-segmented vectors for such viruses. Furthermore, the segmentation of the genome of a naturally non-segmented virus, including NDV, is most likely attenuating the virus, adding an extra-safety measure to the use of such segmented vectors in vaccines for animals or humans (Flanagan E B et al. (2001) J Virol 75:6107-6114). Recombinant segmented vectors for naturally non-segmented negative strand viruses expressing one or more foreign antigens, heterologous proteins and/or immunostimulatory molecules could be used as effective vaccines or therapies against different diseases, including ADS and cancer.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All references cited herein are incorporated herein by reference in the entirety for all purposes.

What is claimed is:

1. A genetically engineered segmented recombinant negative-strand RNA virus of the Paramyxoviridae family of the Mononegavirales order wherein a naturally non-segmented virus having a naturally non-segmented RNA genome is engineered to have a segmented RNA genome comprising two or more distinct viral genomic RNA segments that collectively provide the viral template and encode the required functional transcriptional units of said RNA virus on distinct segmented RNA molecules.

2. The virus of claim 1 which has an attenuated phenotype.

3. The virus of claim 1 which is engineered to encode a heterologous polypeptide selected from the group of a viral antigen, bacterial antigen, parasite antigen, tumor antigen, oncogene or modified oncogene, ligand or receptor binding protein, therapeutic protein, growth factor or immunomodulatory molecule.

4. The virus of claim 3 which is a chimeric virus engineered to encode a viral antigen.

5. The virus of claim 4 in which the viral antigen is derived from a virus selected from the group of human immunodeficiency virus, Newcastle disease virus, influenza, respiratory syncytial virus, Marek's disease virus, infectious bursal disease virus, infectious bronchitis virus, infectious bursitis virus, chicken anemia virus, infectious laryngotracheitis virus, avian luekosis virus, reticuloendotheliosis virus, avian influenza virus, rabies virus, feline distemper virus, vesicular stomatitis virus, rinderpest virus, and swinepox virus.

6. A therapeutic formulation comprising the recombinant negative-strand RNA virus of claim 1, which virus is engineered to encode a heterologous polypeptide, and a pharmaceutically acceptable excipient or vehicle.

* * * * *

UNITED STATES PATENT AND TRADEMARK OFFICE
CERTIFICATE OF CORRECTION

PATENT NO.       : 8,709,442 B2                                   Page 1 of 1
APPLICATION NO. : 10/505613
DATED            : April 29, 2014
INVENTOR(S)      : Garcia-Sastre et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 853 days.

Signed and Sealed this

Twenty-ninth Day of September, 2015

Michelle K. Lee
*Director of the United States Patent and Trademark Office*